United States Patent [19]

Fleck et al.

[11] 4,020,109

[45] Apr. 26, 1977

[54] STABILIZING ALKANALS

[75] Inventors: Raymond N. Fleck, West Covina; Donald C. Young, Fullerton, both of Calif.

[73] Assignee: Union Oil Company of California, Brea, Calif.

[22] Filed: Dec. 26, 1972

[21] Appl. No.: 318,176

[52] U.S. Cl. .......................................... 260/601 R
[51] Int. Cl.² ...................................... C07C 47/02
[58] Field of Search ............................... 260/601 R

[56] References Cited

UNITED STATES PATENTS

| 2,170,625 | 8/1939 | Wyler | 260/601 R |
| 2,212,894 | 11/1937 | Allen | 260/601 R |
| 2,413,038 | 12/1946 | Dinwiddie | 260/601 |

OTHER PUBLICATIONS

Cotton et al., Adv. Inorg. Chem., pp. 334, 672, 680, 681, 683, 749 and 750.

Primary Examiner—Donald G. Daus
Assistant Examiner—D. B. Springer
Attorney, Agent, or Firm—Richard C. Hartman; Dean Sandford

[57] ABSTRACT

Polymer formation and aldol condensation by a hydrocarbyl aldehyde is prevented by adding to the aldehyde a trace to minor amount of readily oxidizable metals or cations having oxidation potentials greater than about $-0.2$ volts. In a typical embodiment, a liquid containing a hydrocarbyl aldehyde is inhibited against aldol condensation by incorporating in the liquid from about 0.005 to about 1.0 weight percent thereof of the aforementioned metals or cations.

6 Claims, No Drawings

STABILIZING ALKANALS

DESCRIPTION OF THE INVENTION

The invention relates to a method for the prevention of aldol condensation and polymer formation from a hydrocarbyl aldehyde.

Tarry constituents and high-boiling byproducts are often formed from hydrocarbyl aldehydes. These high-boiling byproducts which result from aldol condensation accumulate in the aldehyde or solution thereof, necessitating its purification.

It is an object of this invention to prevent the formation of high-boiling byproducts in hydrocarbyl aldehydes.

It is an additional object of this invention to provide an inhibitor to reduce the amount of polymer and high-boiling byproducts formed in hydrocarbyl aldehydes.

Other and related objects will be apparent from the following description of the invention.

We have now found that aldol condensation and the formation of tars and high-boiling byproducts from hydrocarbyl aldehydes apparently proceeds by a free radical mechanism. It is believed that this free radical mechanism is initiated or propagated by peroxide radicals formed by reaction with oxygen-containing impurities or contaminants that are unavoidably introduced into the aldehyde or solutions thereof. We have further found that the incorporation in the reaction medium of various metals or metal cations having oxidation potentials more positive than −0.20 volts and, preferably, from −0.20 to +0.41 volts, substantially reduces and prevents aldol condensation and polymer formation. As used herein, values of the oxidation potentials are standard oxidation potentials which refer to the hydrogen-hydrogen ion couple as zero and are expressed for unit activities and a temperature of 25° C.

The various metals that can be used and, for multivalent metals, the cations that can be used, include the following: cadmium ($Cd°$), indium ($In°$), tantalum ($Tl°$), cobalt ($Co°$), nickel ($Ni°$), molybdenum ($Mo°$), tin ($Sn°$), lead ($Pb°$), copper ($Cu°$), chromous ($Cr^{++}$), titanous ($Ti^{++}$), vanadous ($V^{++}$), stannous ($Su^{++}$), and cuprous ($Cu^+$). It is believed that these inhibitors function by providing an oxidizable substrate, i.e., contribute an electron to the free radical initiator or propagating agent of the aldo or polymer condensation. This contribution of an electron pairs the lone electron of the free radical, thereby destroying its activity and results in oxidation of the metal inhibitor to a higher oxidation state.

The activity of the inhibitor in the reaction medium can be maintained during extended, continuous processing or storage by periodically or intermittently reducing the higher oxidation state for the inhibiting metal to its effective low oxidation state of reuse. This can be accomplished by subjecting all or a portion of the liquid containing the inhibitor to a reducing treatment. Typically, temperatures from 30° to about 200° C. and sufficient pressures to maintain the solution in liquid phase can be used for the reducing treatment. Pressures from 1 to about 100 atmospheres, absolute, can be used.

In a preferred embodiment, copper is used as the inhibitor, e.g., a soluble cuprous salt is incorporated in the aldehyde or solution thereof. The cuprous salt is oxidized to a cupric salt by the free radicals which, in the absence of the cuprous salt would initiate aldol or polymer condensation. The resultant cupric salt, however, is a strong oxidizing agent and readily oxidizes carbon monoxide to carbon dioxide with reduction to the cuprous salt, which is thus available for further reaction with free radicals. A suitable reducing treatment, therefore, comprises the treatment of all or a portion of the solution with carbon monoxide. Hydrogen can also be used, if desired, to treat the solution and thereby retain some of the copper salt in the cuprous state. Preferably, a slight amount of water from 0.1 to 50 weight percent of the liquid can be incorporated in the liquid during such treatments to insure the oxidation of the carbon monoxide or hydrogen and reduction of any cupric salts to the effective cuprous inhibitor.

Various hydrocarbyl aldehydes can be inhibited in accordance with the invention. The aldehyde is preferably a liquid, either neat or dissolved in a suitable solvent and the inhibitor is added to the liquid. The aldehyde can be any hydrocarbyl, saturated, aliphatic, monoaldehyde, i.e., an alkanal, having from 2 to about 25 carbons, preferably from 3 to about 20 carbons. The aldehyde can be straight chained or can have various side chains and a branched structure provided that the alpha-carbon have at least one hydrogen. This hydrogen, of course, is necessary to render the aldehyde susceptible to aldol condensation. Examples of suitable aldehydes are: are acetaldehyde, propionaldehyde, butyraldehyde, isobutyraldehyde, pentanal, hexanal, 2-methylpentanal, 2-ethylhexanal, octanal, propylhexanal, decanal, 4,4'-dimethylnonanal, dodecanal, undecanal, 6-propyldecanal, tetradecanal, 7-amyldecanal, hexadecanal, 4-ethyltridecanal, octadecanal-1, 5,5'-dipropyldodecanal-1, etc. Of the preceding, the straight chained aldehydes having from 3 to about 20 carbons are preferred and those having from 3 to about 17 carbons are most preferred for the inhibition treatment by this invention. Mixtures of two or more of these aldehydes can be treated.

The hydrocarbyl aldehyde is treated by addition of the inhibitor under liquid phase conditions and, when the aldehyde is liquid at the addition conditions, it can be treated neat, i.e., in absence of a solvent. If desired, however, the aldehyde can be dissolved in any suitable organic liquid; preferably, organic solvents which are inert to the inhibitor are employed. Examples of suitable solvents which can be used in accordance with our invention include hydrocarbons such as the aromatic, aliphatic or alicyclic hydrocarbons, ethers, esters, ketones, etc.

Examples of suitable hydrocarbons that can be employed as solvents include aromatic hydrocarbons such as benzene, toluene, xylene, ethylbenzene, tetralin, etc.; aliphatic hydrocarbons such as butane, pentane, isopentane, hexane, isohexane, heptane, octane, isooctane, naphtha, gasoline, kerosene, mineral oil, etc.; alicyclic hydrocarbons, e.g., cyclopentane, cyclohexane, methylcyclopentane, decalin, indane, etc.

Various alkyl and aryl ketones can also be employed as the solvent, e.g., acetone, methylethyl ketone, diethyl ketone, diisopropyl ketone, ethyl-n-butyl ketone, methyl-n-amyl ketone, cyclohexanone, diisobutyl ketone, etc.

Ethers can also be employed as the solvent, e.g., diisopropyl ether, di-n-butyl ether, ethylene glycol diisobutyl ether, methyl-o-tolyl ether, ethylene glycol dibutyl ether, diisoamyl ether, methyl p-tolyl ether, methyl m-tolyl ether, dichloroethyl ether, ethylene glycol diisoamyl ether, diethylene glycol diethyl ether, ethylbenzyl ether, diethylene glycol diethyl ether, diethylene glycol dimethyl ether, ethylene glycol dibutyl ether, ethylene glycol diphenyl ether, triethylene glycol diethyl ether, diethylene glycol di-n-hexyl ether, tetraethylene glycol dimethyl ether, tetraethylene glycol dibutyl ether, etc.

Various esters can also be employed as the solvent, e.g., ethyl formate, methyl acetate, ethyl acetate, n-propyl formate, ispropyl acetate, ethyl propionate, n-propyl acetate, sec-butyl acetate, isobutyl acetate, ethyl n-butyrate, n-butyl acetate, isoamyl acetate, n-amyl acetate, ethyl formate, ethylene glycol diacetate, glycol diformate, cyclohexyl acetate, furfuryl acetate, isoamyl n-butyrate, diethyl oxalate, isoamyl isovalerate, methyl benzoate, diethyl maleate, valerolactone, ethyl benzoate, methyl salicyclate, n-propyl benzoate, n-dibutyl oxalate, n-butyl benzoate, diisoamyl phthalate, dimethyl phthalate, diethyl phthalate, benzyl benzoate, n-dibutyl phthalate, etc. A preferred class of ester solvents includes the lactones, e.g., butyrolactone, valerolactone, and their derivatives having lower ($C_1$–$C_5$) alkyl substituents. Alcohols can also be employed as a solvent. Preferably tertiary alcohols are employed since these materials are substantially non-reactive of aldehydes.

Examples of alcohols that can be employed as solvents include the aliphatic and alicyclic alcohols such as methanol, ethanol, isopropanol, butanol, t-butanol, t-amyl alcohol, hexanol, cyclohexanol, etc.

The inhibitor which can be incorporated in the reaction medium to prevent or to reduce the amount of aldol condensation polymers and byproducts can be a metal or metal cation having an oxidation potential more positive than −0.20 volts and, preferably, having an oxidation potential between −0.20 and +0.41 volts. Examples of suitable inhibitors and their oxidation potentials are the following:

| | | |
|---|---|---|
| $Cd^\circ$ | $\rightleftharpoons$ $Cd^{++} + 2e$ | +0.403 |
| $In^\circ$ | $\rightleftharpoons$ $In^{+++} + 3e$ | +0.342 |
| $Tl^\circ$ | $\rightleftharpoons$ $Tl^+ + 1e$ | +0.336 |
| $Co^\circ$ | $\rightleftharpoons$ $Co^{++} + 2e$ | +0.277 |
| $Ni^\circ$ | $\rightleftharpoons$ $Ni^{++} + 2e$ | +0.250 |
| $Mo^\circ$ | $\rightleftharpoons$ $Mo^{+++} + 3e$ | +0.2 |
| $Sn^\circ$ | $\rightleftharpoons$ $Sn^{++} + 2e$ | +0.136 |
| $Pb^\circ$ | $\rightleftharpoons$ $Pb^{++} + 2e$ | +0.126 |
| $Cu^\circ$ | $\rightleftharpoons$ $Cu^+ + 1e$ | −0.337 |
| $Cr^{++}$ | $\rightleftharpoons$ $Cr^{+++} + 1e$ | +0.41 |
| $Ti^{++}$ | $\rightleftharpoons$ $Ti^{+++} + 1e$ | +0.37 |
| $V^{++}$ | $\rightleftharpoons$ $V^{+++} + 1e$ | +0.255 |
| $Sn^{++}$ | $\rightleftharpoons$ $Sn^{++++} + 2e$ | −0.15 |
| $Cu^+$ | $\rightleftharpoons$ $Cu^{++} + 1e$ | −0.153 |

The metal can be incorporated in the reaction medium in a low valency state, preferably as a soluble salt or can be added as an oxide or finely divided metal. The particular anion associated with the salt is chemically not significant and any anion which is chemically inert to the aldehyde can be used. To insure activity of the aldol inhibitors, the inhibitor should be soluble and, therefore, the anion should not precipitate the inhibitor. Suitable anions from which a candidate can be chosen include: nitrate, sulfate, halide, carboxylate of $C_1$ to $C_{12}$ acids, alkyl and aryl sulfonates, etc.

Examples of suitable salts include: cuprous chloride, cuprous nitrate, cuprous sulfate, cuprous bromide, stannous chloride, stannous citrate, stannous iodide, stannous sulfate, vanadous chloride, vanadous fluoride, vanadous sulfate, titanous bromide, titanous chloride, titanous sulfate, titanous iodide, chromous sulfate, chromous bromide, chromous chloride, chromous acetate, chromous bromide, etc. When the metal or an oxide is added, it is preferably added in a finely divided state since it had a very limited solubility and a fine degree of subdivision will provide adequate surface area for inhibition. Generally, solids passing about a 20 mesh screen and, preferably, passing a 100 mesh screen are used. Other forms such as metal shavings, foil, wire or rod can also be used. Examples of suitable oxides are: cuprous oxide, chromous oxide, stannous oxide, vanadous oxide, titanium mono-oxide, etc.

The aforementioned inhibitor of the aldol condensation and polymer formation is incorporated in the aldehyde or its solution to provide, calculated as the metal, from about 0.001 to about 2.5 weight percent; preferably from about 0.005 to about 1.0; and most preferably from about 0.01 to about 0.1 weight percent of the aldehyde present. The preferred inhibitors are salts of the metal cations rather than the free metals since the salts have solubility in the reaction medium at both the reduced and oxidized states.

EXAMPLE

The inhibiting effect of a reduced metal, cadmium, was determined by purifying n-butyraldehyde by distillation through a 40-plate column to remove extraneous material and some of the potential aldol condensation initiators. A sample of one milliliter of the purified aldehyde was placed in a one inch section of 3 percent chromium, 6 percent nickel, stainless steel tubing and capped. Another sample was similarly prepared, however, about 0.05 grams of cadmium metal shavings were placed in the second metal tubing before capping. The two tubes were stored about 45 hours in a bath maintained at 110° C. The tubes were removed and analyzed for polymers by gas chromatography. There was only 30 percent polymer in the liquid from the tube containing the cadmium metal and 70 weight percent in the liquid from the tube having no cadmium metal contained therein.

The experiment was repeated using cuprous chloride as the inhibitor by charging about 0.01 gram of cuprous chloride to a tube containing about 1 gram of n-butyraldehyde which was purified by redistillation from ferrous sulfate to remove peroxide. The flask was stored over night at 110° C, together with a similar tube of similarly purified butyraldehyde containing no additive. After about 22 hours of aging, the tube containing no cuprous chloride had 8.2 percent polymer while that containing the cuprous chloride had 6.1 percent polymer.

Substantially the same results are achieved when the reaction medium is charged with 5.0 grams of titanous fluoride, or 2 grams of stannous chloride, or 8.0 grams of molybdenous acetate, or 2.5 grams of vanadous chloride.

The preceding examples are solely to illustrate a mode of practice of the invention and are not to be construed as unduly limiting thereof. Instead, it is intended that the invention be defined by the steps and reagents and their obvious equivalents set forth in the following claims:

We claim:

1. The method of inhibiting the aldol condensation of an alkanal having from 2 to about 25 carbons and at least one hydrogen on the alpha carbon, in the absence of solvent or in the presence of an organic solvent inert to the inhibitor hereinafter defined, which comprises admixing therewith an inhibitor selected from the group consisting of:
  a. finely divided elemental metals having particle sizes sufficiently small to pass a 100 mesh screen and selected from cadmium, indium, thallium, cobalt, nickel, molybdenum, tin, lead, copper and combinations thereof;
  b. the finely divided oxides of multivalent metal cations selected from chromous, titanous, vanadous, stannous, cuprous cations and combinations thereof; and
  c. salts of oxidizable multivalent metal cations selected from chromous, titanous, vanadous, stannous and cuprous cations, and anions selected from nitrate, sulfate, halide, $C_1$–$C_{12}$ carboxylate and alkyl and aryl sulfonate anions and combinations thereof;

said metals and cations having standard oxidation potentials between −0.20 and +0.41 volts, in an amount from 0.005 to 1.0 weight percent expressed as the metal and based on said alkanal.

2. The method of claim 1 further comprising admixing carbon monoxide with said alkanal, and wherein said alkanal is a straight chain alkanal having from 3 to about 17 carbons.

3. The method of claim 1 wherein said alkanal is straight chained.

4. The stabilized composition comprising a liquid phase alkanal stabilized against aldol condensation comprising an alkanal having from 2 to about 25 carbons and at least one hydrogen on the alpha carbon, in the absence of solvent or in the presence of an organic solvent inert to the inhibitor hereinafter defined, and an aldol condensation inhibitor selected from the group consisting of:
  a. finely divided elemental metals having particle sizes sufficiently small to pass a 100 mesh screen and selected from cadmium, indium, thallium, cobalt, nickel, molybdenum, tin, lead, copper and combinations thereof;
  b. the oxides of multivalent metal cations selected from chromous, titanous, vanadous, stannous, cuprous cations and combinations thereof; and
  c. salts of oxidizable multivalent metal cations selected from chromous, titanous, vanadous, stannous and cuprous cations, and anions selected from nitrate, sulfate, halide, $C_1$–$C_{12}$ carboxylate and alkyl and aryl sulfonate anions and combinations thereof;

said metals and cations having standard oxidation potentials between minus 0.20 and plus 0.41 volts, and wherein the concentration of said inhibitor in said composition is between about 0.005 and about 1.0 weight percent expressed as the metal and based on said alkanal.

5. The composition of claim 4 wherein said inhibitor is selected from the group consisting of cadmium metal and cuprous chloride.

6. The method of inhibiting the aldol condensation of an alkanal having from 2 to about 25 carbons and at least one hydrogen on the alpha carbon, in the absence of solvent or in the presence of an organic solvent inert to the inhibitor hereinafter defined, which comprises admixing therewith an inhibitor selected from the group consisting of cadmium metal and cuprous chloride in an amount of 0.005 to 1 weight percent expressed as the metal and based on said alkanal.

* * * * *